(12) United States Patent  
Jaramillo-Botero et al.

(10) Patent No.: US 9,234,882 B2  
(45) Date of Patent: Jan. 12, 2016

(54) TRANSLOCATION AND NUCLEOTIDE READING MECHANISMS FOR SEQUENCING NANODEVICES

(71) Applicant: CALIFORNIA INSTITUTE OF TECHNOLOGY, Pasadena, CA (US)

(72) Inventors: Andres Jaramillo-Botero, Pasadena, CA (US); William A. Goddard, III, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 14/576,148

(22) Filed: Dec. 18, 2014

(65) Prior Publication Data

US 2015/0101933 A1  Apr. 16, 2015

Related U.S. Application Data

(62) Division of application No. 13/621,735, filed on Sep. 17, 2012, now Pat. No. 8,951,727.

(60) Provisional application No. 61/536,381, filed on Sep. 19, 2011, provisional application No. 61/536,327, filed on Sep. 19, 2011.

(51) Int. Cl.
*G01N 33/48* (2006.01)
*G01N 33/487* (2006.01)
*H01L 51/05* (2006.01)
*H01L 51/00* (2006.01)
*G01N 27/414* (2006.01)
(Continued)

(52) U.S. Cl.
CPC .......... *G01N 33/48721* (2013.01); *B82Y 15/00* (2013.01); *C12Q 1/6869* (2013.01); *G01N 27/4145* (2013.01); *G01N 27/44704* (2013.01); *G01N 33/1826* (2013.01); *H01L 51/0048* (2013.01); *H01L 51/055* (2013.01); *H01L 51/0558* (2013.01); *G01N 33/18* (2013.01)

(58) Field of Classification Search
CPC .................. C12Q 1/6869; B82Y 15/00; G01N 27/44704; G01N 33/1829; G01N 33/18
See application file for complete search history.

(56) References Cited

U.S. PATENT DOCUMENTS

2003/0080042 A1* 5/2003 Barth et al. ............... 210/321.84
2003/0178617 A1   9/2003 Appenzeller et al.
(Continued)

FOREIGN PATENT DOCUMENTS

WO   2009/035647   3/2009
WO   2010/066794   6/2010

OTHER PUBLICATIONS

Branton, D. et al., *The potential and challenges of nanopore sequencing*, Nature Biotechnology, Oct. 2008, vol. 26, No. 10, pp. 1146-1153.

(Continued)

*Primary Examiner* — J. Christopher Ball
(74) *Attorney, Agent, or Firm* — Steinfl & Bruno LLP

(57) ABSTRACT

By driving molecules electrophoretically through a nanopore, single molecule detection can be achieved. To enhance translocational control, functionalized and non-functionalized electrodes are strategically placed around or above a nanopore. Changes in transmission spectra and input voltage detected by electrodes allow accurate identification of single molecules as they pass through a nanopore.

11 Claims, 13 Drawing Sheets

(51) Int. Cl.
*B82Y 15/00* (2011.01)
*C12Q 1/68* (2006.01)
*G01N 27/447* (2006.01)
*G01N 33/18* (2006.01)

(56) References Cited

U.S. PATENT DOCUMENTS

| | | | |
|---|---|---|---|
| 2004/0007740 A1 | 1/2004 | Abstreiter et al. | |
| 2005/0170347 A1 | 8/2005 | Miyahara et al. | |
| 2007/0190543 A1 | 8/2007 | Livak | |
| 2008/0032294 A1 | 2/2008 | Kawarada et al. | |
| 2008/0063566 A1 | 3/2008 | Matsumoto et al. | |
| 2008/0171316 A1 | 7/2008 | Golovchenko et al. | |
| 2009/0136958 A1 | 5/2009 | Gershow et al. | |
| 2010/0084276 A1 | 4/2010 | Lindsay | |
| 2010/0327847 A1 | 12/2010 | Leiber et al. | |
| 2011/0133255 A1 | 6/2011 | Merz | |
| 2011/0168562 A1 | 7/2011 | Nuckolls et al. | |
| 2011/0223652 A1* | 9/2011 | Peng et al. | 435/287.2 |
| 2011/0279125 A1 | 11/2011 | Bedell et al. | |

OTHER PUBLICATIONS

Novoselov, K.S., et al., *Electric field effect in atomically thin carbon films*. Science, 2004, 306(5696): p. 666-669.
Chen, Z.H., et al., *Graphene nano-ribbon electronics*. Physica E-Low-Dimensional Systems & Nanostructures, 2007, 40(2): p. 228-232, (pp. 1-6).
Ikeda, T. et al., *Toward Electrochemically Controllable Tristable Three-Station [2] Catenanes*, Chem. Asian J., 2007, vol. 2, pp. 76-93.
Li, J.L., et al., *DNA molecules and configurations in a solid-state nanopore microscope*. Nature Materials, 2003, 2(9): p. 611-615.
Li, J., et al., *Nanoscale Ion-beam sculpting at nanometre length scales*. Nature, 2001, 412(6843): p. 166-169, (pp. 1-11).
Meller, A. et al., *Single molecule measurements of DNA transport through a nanopore*, Electrophoresis, 2002, vol. 23, pp. 2583-2591.
Dekker, C., *Solid-state nanopores*. Nature Nanotechnology, 2007, 2(4): p. 209-215.
Gorjizadeh, N. and Y. Kawazoe, *Chemical Functionalization of Graphene Nanoribbons*. Journal of Nanomaterials, 2010, pp. 1-7.
Hugel, T., et al., *Single-molecule optomechanical cycle*. Science, 2002, 296(5570): p. 1103-1106.
Umapathy,N.B.S., *Early time dynamics of trans-azobenzene isomerization in solution from resonance Raman intensity analysis*. Journal of Chemical Physics, 1997, 107(19): p. 7849-7858.
Krapf, D., et al., *Fabrication and characterization of nanopore-based electrodes with radii down to 2 nm*. Nano Letters, 2006, 6(1): p. 105-109.
Zandbergen, H.W., et al., *Sculpting nanoelectrodes with a transmission electron beam for electrical and geometrical characterization of nanoparticles*. Nano Letters, 2005, 5(3): p. 549-553.
Merino, E., *Synthesis of azobenzenes: the coloured pieces of molecular materials*. Chemical Society Reviews, 2011, 40(7): p. 3835-3853.
Han, M., et al., *Light-driven molecular switches in azobenzene self-assembled monolayers: effect of molecular structure on reversible photoisomerization and stable cis state*. Chemical Communications, 2010, 46(20): p. 3598-3600.
Uchida, K., et al., *Photoinduced reversible formation of microfibrils on a photochromic diarylethene microcrystalline surface*. Angewandte Chemie-International Edition, 2006, 45(39): p. 6470-6473.
Min, S.K., et al., *Fast DNA sequencing with a graphene-based nanochannel device*. Nature Nanotechnology, 2011, 6(3): p. 162-165.
Gillis, H.P., et al., *Low-Energy Electron-Enhanced Etching of Si(100) in Hydrogen Helium Direct-Current Plasma*. Applied Physics Letters, May 8, 1995. 66(19): p. 2475-2477.
Gillis, H.P., et al., *Patterning III-N semiconductors by low energy electron enhanced etching (LE4)*. Mrs Internet Journal of Nitride Semiconductor Research, 1999, 4: p. art. No. G8.2.

Nguyen, T.D., et al., *Wafer-Scale Nanopatterning and Translation into High-Performance Piezoelectric Nanowires*. Nano Letters, 2010, 10(11): p. 4595-4599.
Maune, H.T., et al., *Self-assembly of carbon nanotubes into two-dimensional geometries using DNA origami templates*. Nature Nanotechnology, 2010, 5(1): p. 61-66 (pp. 1-6).
Park, J.Y., *Carbon nanotube field-effect transistor with a carbon nanotube gate electrode*. Nanotechnology, 2007, 18(9).
Svensson, J., et al., *A carbon nanotube gated carbon nanotube transistor with 5 ps gate delay*. Nanotechnology, 2008, 19(32).
Stokbro, K., et al., *Semiempirical model for nanoscale device simulations*. Physical Review B, 2010, 82(7), pp. 1-8.
Cerda, J. and F. Soria, *Accurate and transferable extended Huckel-type tight-binding parameters*. Physical Review B, 2000, 61(12): p. 7965-7971.
Beaucage, S.L. and M.H. Caruthers, *Deoxynucleoside Phosphoramidites—a New Class of Key Intermediates for Deoxypolynucleotide Synthesis*. Tetrahedron Letters, 1981, 22(20): p. 1859-1862.
Wind, S.J., et al., *Vertical scaling of carbon nanotube field-effect transistors using top gate electrodes* (vol. 80, p. 3817, 2002). Applied Physics Letters, 2002, 81(7): p. 1359-1359.
Chen, Z. et al., *Externally assembled gate-all-around carbon nanotube field-effect transistor*. IEEE Electron Device Letters, Feb. 2008. 29(2): p. 183-185.
Singh, S.K., et al., *LNA (locked nucleic acids): synthesis and high-affinity nucleic acid recognition*, Chemical Communications, 1998(4): p. 455-456.
Koshkin, A.A., et al., *LNA (Locked Nucleic Acids): Synthesis of the adenine, cytosine, guanine, 5-methylcytosine, thymine and uracil bicyclonucleoside monomers, oligomerisation, and unprecedented nucleic acid recognition*, Tetrahedron, 1998. 54(14): p. 3607-3630.
PCT International Search Report for PCT Application PCT/US2012/055787 filed on Sep. 17, 2012. Mail date: Feb. 26, 2013.
PCT Written Opinion for PCT Application PCT/US2012/055787 filed on Sep. 17, 2012 Mail date: Feb. 26, 2013.
PCT International Search Report for PCT Application PCT/US2012/055796 filed on Sep. 17, 2012 Mail date: Feb. 26, 2013.
PCT Written Opinion for PCT Application PCT/US2012/055796 filed on Sep. 17, 2012 Mail date: Feb. 26, 2013.
Aksimentiev, A., et al., "Microscopic Kinetics of DNA Translocation through Synthetic Nanopores." (2004). *Biophys. J.* 87:2086-2097.
Buttiker, M., et al., "Generalized Many-Channel Conductance Formula with Application to Small Rings." (1985). *Phys. Rev. B.* 31(10):6207-6215.
Buttiker, M., et al., "Magnetic Field Asymmetry in the Multichannel Landauer Formula." (1985). *J. Phys. C.* 18: L467-L472.
Chang, H., et al., "DNA-Mediated Fluctuations in Ionic Current Through Silicon Oxide Nanopore Channels" (2004). *Nano Letters*, 4 (8):1551-1556.
Cornell, W., et al., "A Second Generation Force Field for the Simulation of Proteins, Nucleic Acids, and Organic Molecules." (1995). *J. Am. Chem. Soc.* 117:5179-5197.
Deng, W., et al., "Bifunctional Anchors Connecting Carbon Nanotubes to Metal Electrodes for Improved Nanoelectronics." (2007). *J Am. Chem.* 129:9834-9835.
Deng, W., et al., "An Electrochemical Color-Switchable RGB Dye: Tristable [2] Catenane." (2005). *J. Am. Chem. Soc.* 127:15994-15995.
Deng, W., et al., "Mechanism of the Stoddart-Health Bistable Rotaxane Molecular Switch." (2004). *J. Am Chem. Soc.* 126:13562-13563.
Deng, W., "Computational Simulation at Molecular Electronic and Molecular Electromechanical System." (2004) Abstracts of JACS 225: U708-709.
Flood, A., et al., "Meccano on the Nanoscale-A Blueprint for Making Some of the World's Tiniest Machines." (2004). *Aust. J. Chem.* 57:301-322.
Harrison, D., et al., "Micromachining a Miniaturized Capillary Electrophoresis-Based Chemical Analysis System on a Chip." (1993). *Science*. 261:895-897.
Heng, J., et al., "Stretching DNA Using the Electric Field in a Synthetic Nanopore." (2005). *Nano Letters*. 5(10):1883-1888.

(56) References Cited

OTHER PUBLICATIONS

Heng, J., et al., "The Electromechanics of DNA in a Synthetic Nanopore." (2006). *Biohpys. J.* 90:1098-1106.
Heng, J., et al., "Stretching DNA using an Artificial Nanopore." (2006) University of Illinois Urbana Champaign, Urbana, IL, USA.
Kasianowicz, J., et al., "Characterization of Individual Polynucleotide Molecules using a Membrane Channel." (1996). *Proc. Natl. Acad. Sci. USA* 93:13770-13773.
Kim, Y., et al., "Possible Performance Improvement in [2]catenane Molecular Electronic Switches." (2006). *Applied Phys. Letters* 88:163112-1-163112-3.
Matsuda, Y., et al., "Improving Contact Resistance at the Nanotube-Cu Electrode Interface Using Molecular Anchors." (2008). *J. Phys. Chem.* 112:11042-11049.
Matsuda, Y., et al., "Contact Resistance Properties between Nanotubes and Various Metals from Quantum Mechanics." (2007). *J. Phys. Chem. C* 111:11113-11116.
Mayo, S., et al., "DREIDING: A Generic Field for Molecular Simulations." (1990). *J. Phys. Chem.* 94:8897-8909.
Merchant, C., et al., "DNA Translocation through Graphene Nanopores." (2010). *Nano Lett.* 10:2915-2921.
Polonsky, S., et al., "Nanopore in metal-dielectric Sandwich for DNA Position Control." (2007). *Appl. Phys. Lett.* 91:153103-1-153103-3.
Postma, H., "Rapid Sequencing of Individual DNA Molecules in Graphene Nanogaps." (2010). *Nano Lett.* 10:420-425.
Simpson, P., "High-throughput Genetic Analysis using Microfabricated 96-Sample Capillary Array Electrophoresis Microplates." (1998). *Proc. Natl. Acad. Sci. USA* 95:2256-2261.
Vercoutere, W., et al., "Discrimination Among Individual Watson-Crick Base Pairs at the Termini of Single DNA Hairpin Molecules." (2003). *Nucleic Acids Research* 31:1311-1318.
Wendel, J., et al., "The Hessian Biased Force Field for Silicon Nitride Ceramics: Predictions of Thermodynamic and Mechanical Properties for $\alpha$- and $\beta$-$Si_3N_4$." (1992). *J. Chem. Phys.* 97(1):5048-5062.
Winters-Hilt, S., et al., "Highly Accurate Classification of Watson-Crick Basepairs on Termini of Single DNA Molecules." (2003). *Biophys. J.* 84:967-976.
Woolley, A., et al., "Ultra-High Speed DNA Sequencing Using Capillary Electrophoresis Chips." (1995). *Anal. Chem.* 67:3676-3680.
Yam, C., et al., "Dynamic Admittance of Carbon Nanotube-Based Molecular Electronic Devices and Their Equivalent Electric Circuit." (2008). *Nanotechnology.* 19:1-7.
Restriction Requirement issued for U.S. Appl. No. 13/621,735, filed on Sep. 17, 2012 in the name of Andres Jaramillo-Boteo. date issued: Sep. 11, 2014.
Non-Final Office Action issued for U.S. Appl. No. 13/621,735, filed on Sep. 17, 2012 in the name of Andres Jaramillo-Boteo. date issued: Sep. 25, 2014.
Notice of Allowance issued for U.S. Appl. No. 13/621,735, filed on Sep. 17, 2012 in the name of Andres Jaramillo-Boteo. date issued: Dec. 12, 2014.
Vlassiouk et al. "Versatile ultrathin nanoporous silicon nitride membranes" Proc. Nat. Acad. Sci. vol. 106, No. 50, Dec. 2009, pp. 21039-21044.
International Preliminary Report on Patentability for PCT Application No. PCT/US2012/055796 filed Sep. 17, 2012 on behalf of California Institute of Technology. Mailed on Mar. 25, 2014.
International Preliminary Report on Patentability for PCT Application No. PCT/US2012/055787 filed Sep. 17, 2012 on behalf of California Institute of Technology. Mailed on Mar. 25, 2014.
Restriction Requirement issued for U.S. Appl. No. 13/621,745, filed on Sep. 17, 2012 in the name of Andres Jaramillo-Boteo. Date issued: Dec. 17, 2014.
Non-Final Office Action issued for U.S. Appl. No. 13/621,745, filed on Sep. 17, 2012 in the name of Andres Jaramillo-Boteo. date issued: Mar. 4, 2015.
Notice of Allowance issued for U.S. Appl. No. 13/621,745 filed on Sep. 17, 2012 in the name of Andres Jaramillo-Boteo. date issued: Jun. 9, 2015.

\* cited by examiner

*trans isomer*  *cis isomer*

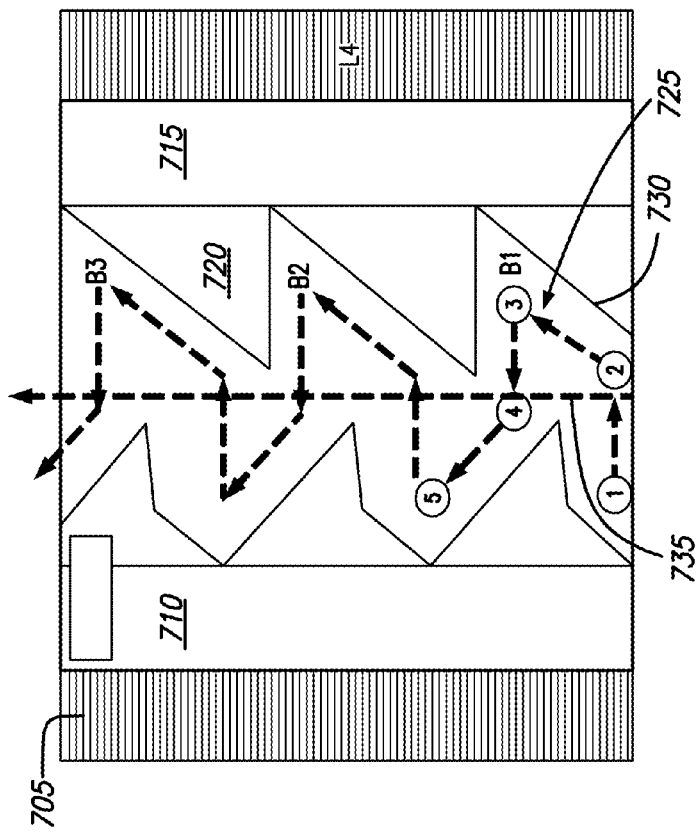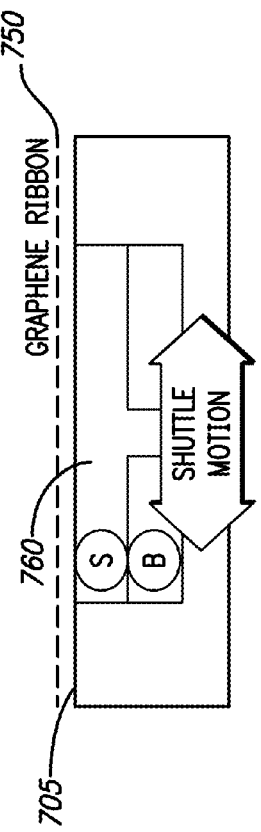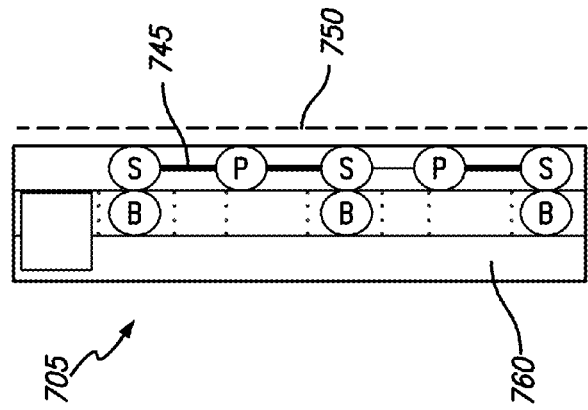

TRANSLOCATION AND NUCLEOTIDE READING MECHANISMS FOR SEQUENCING NANODEVICES

CROSS REFERENCE TO RELATED APPLICATIONS

The present application is a U.S. divisional application of U.S. patent application Ser. No. 13/621,735 filed on Sep. 17, 2012, which, in turn, claims priority to U.S. Provisional Application 61/536,327 filed on Sep. 19, 2011, entitled "ssDNA Translocation Control and Nucleotide Sequencing Nano-Device Mechanisms" and U.S. Provisional Application 61/536,381 filed on Sep. 19, 2011, entitled "ssDNA Translocation Control and Nucleotide Sequencing Nano-Device Mechanisms", both of which are incorporated herein by reference. The present application is also related to U.S. patent application Ser. No. 13/621,745 filed on Sep. 17, 2012, entitled "Using a Field Effect Device for Identifying Translocating Charge-Tagged Molecules in a Nanopore Sequencing Device", which is also incorporated herein by reference.

FIELD

The present teachings relate to devices that may be used to translocate and identify molecules through a nanopore. More specifically, the present disclosure relates to translocation and nucleotide reading mechanisms for DNA/RNA sequencing nanodevices.

BACKGROUND

Inexpensive, time-efficient full genome sequencing, will enable prediction and impact-minimization of diseases through personalized, preventive medicine. Full genome sequencing is of great importance for research into the basis of genetic disease, and access to a large database of individualized genome sequences will facilitate cross-correlating gene-type to gene-function. One means to achieve rapid, full genome sequencing is to employ nanopore devices, which can provide single-molecule detection and identification without the need to amplify or label the nucleic acids. Three main problems facing genome sequencing with nanopore devices today are pore capture, translocation control and base identification.

SUMMARY

According to a first aspect of the disclosure, a molecule capturing device comprising a solid state membrane containing nanopores, each nanopore defining a space within which molecules can pass and be detected, each nanopore comprising electrodes, the electrodes being functionalized with a material capable to capture a molecule passing through the nanopore by way of hydrogen bonding between the material and the molecules.

According to a second aspect of the disclosure, a molecule capturing device comprising a solid state membrane containing nanopores, each nanopore defining a space within which molecules can pass and be detected, each nanopore comprising at least one pair of electrodes, the at least one pair of electrodes are attached to the walls inside the pore, being functionalized with an chemical arrangement adapted to undergo stereochemical changes, and capable of assuming a first stereochemical configuration where a molecule passing through the nanopore is slowed and a second stereochemical configuration where a molecule passing through the nanopore moves freely.

According to a third aspect of the disclosure, a device to translocate molecules, comprising: a first molecule channel along which translocation of the molecules is adapted to occur along a first direction; and teeth moveable back and forth in a teeth direction substantially perpendicular to the first direction, wherein movement back and forth of the first set of teeth in the teeth direction causes the translocation of the molecules in the first molecule channel along the first direction.

The details of one or more embodiments of the disclosure are set forth in the accompanying drawings and the description below. Other features and objects will be apparent from the description and drawings, and from the claims.

BRIEF DESCRIPTION OF DRAWINGS

The accompanying drawings, which are incorporated into and constitute a part of this specification, illustrate one or more embodiments of the present disclosure and, together with the detailed description and examples sections, serve to explain the principles and implementations of the disclosure.

FIG. 2A shows hydrogen bonding of a pair of grabbers binding to Adenine. Also in FIG. 2A, a nanopore is depicted as a circular perforation in a gray membrane (SiN-based or other material). FIG. 2B shows hydrogen bonding of Thymine and a base and phosphate grabber (without depiction of the nanopore and the top and bottom electrodes and hydrogen bond grabbers).

FIGS. 4A and 4B show an azobenzene compound. In particular, FIG. 4A show cis-/trans-isomers of azobenzene, while FIG. 4B shows the compound anchored to a gold surface.

FIG. 6A shows a photoisomerizable array of azobenzenes that covers the surface of an intra-nanopore wall to control DNA/RNA translocation through the nanopore device. FIG. 6B shows the cis- and trans-azobenzene states that can be reversibly changed by a change in radiation frequency, which results in either a longer or more contracted form of the compound.

FIGS. 7A-7C show a piezoelectric moveable arrangement ("nanoshuttle") to control the translocation of ssDNA or ssRNA molecules. In particular, FIG. 7A shows a top view of a piezoelectric nanoshuttle that moves left and right with perpendicular motion to a ssDNA/RNA translocation direction (up/down motion relative to page). FIGS. 7B and 7C show cross-sectional and front views of the nanoshuttle illustrated in FIG. 7A.

DETAILED DESCRIPTION

The exemplary embodiments according to the present disclosure describe devices that provide for translocation and/or electron current readings of individual molecules for the purpose of identification.

As described in the present disclosure, a nanopore is a very small hole with a range of approximately 1.5-4 nanometers in a synthetic silicon-based (or other material) membrane, which allows molecules the size of DNA or RNA to pass one nucleic acid base at a time through the nanopore. A nanopore sequencing device is a device that uses solid-state nanopore membranes to achieve its function. A nanogap is defined as the space spanning a nanopore. A nanoshuttle is a nanometer sized mechanical shuttle that enables traverse translocation of DNA or RNA strands as well as polymer chains with short side chains.

As further described in the present disclosure, a functionalized electrode is an electrode that has a separate component with a different function to supplement the conductive and molecule binding properties of the electrode. An electrode can be functionalized with a chemical group or compound attached to the electrode, where the functional group or compound is able to retain its function/activity independent of the current passing through the electrode.

As further described in the present disclosure, a phosphate grabber (PG) is a chemical group that can be functionalized to an electrode that couples with a nucleotide's phosphate moiety. On the other hand, a base grabber (BG) is a chemical group that can be functionalized to an electrode that couples with a nucleotide's base moiety.

As further described in the present disclosure, a molecular ratchet is a device that allows linear or rotary motion in only one direction of molecules as well as halting or braking the linear/rotary motion of molecules. Use of a molecular ratchet can result in a stop-go-stop control of a molecule's translational or rotational motion as the molecule moves through a nanopore.

Figure 1:
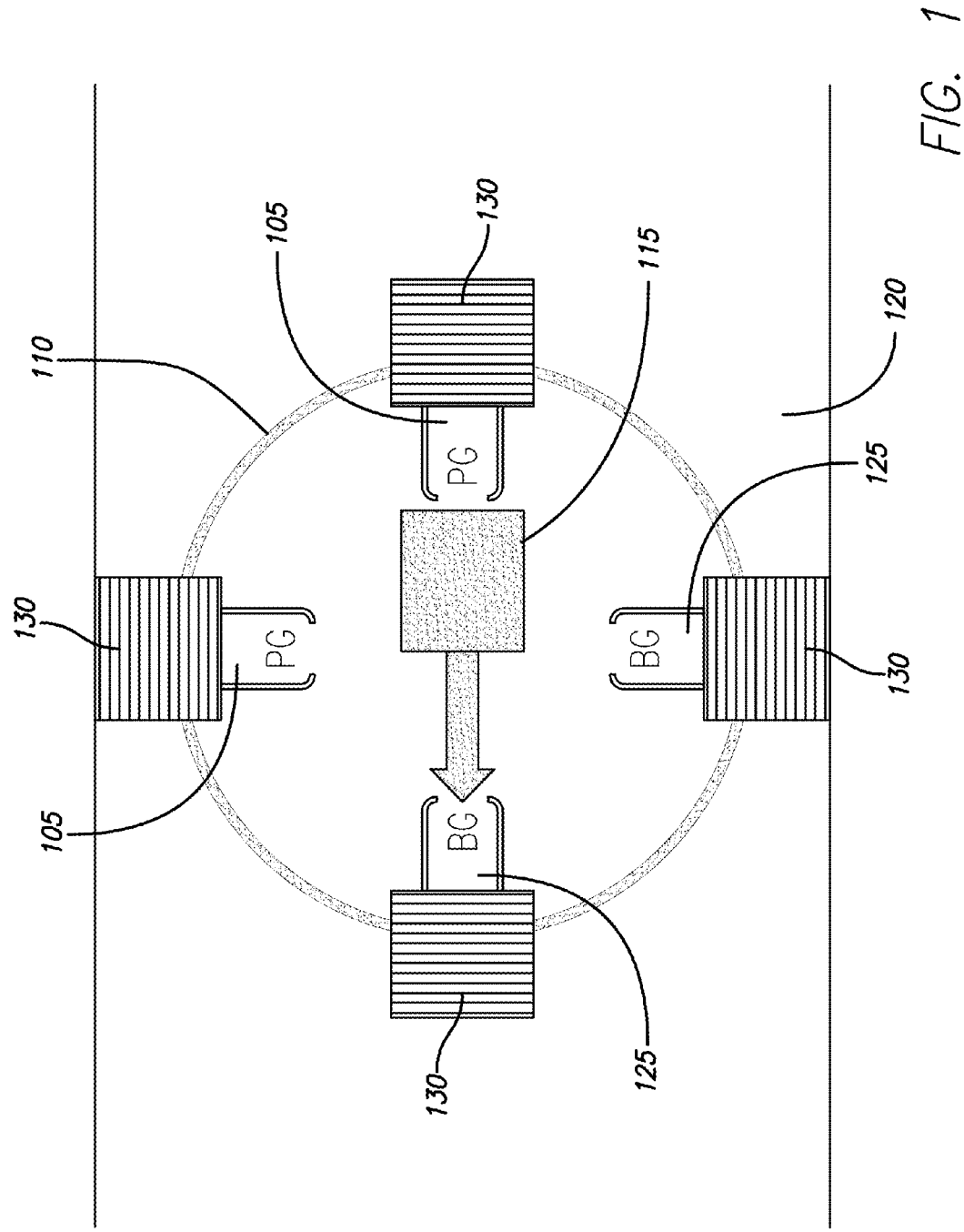
FIG. 1 shows an exploded view of an arrangement of phosphate grabbers (PG) and base grabbers (BG) around a nanopore on a solid-state membrane in order to capture and translocate molecules, such as DNA molecules.

FIG. 1 is a schematic diagram illustrating a base and backbone phosphate hydrogen-bond grabber arrangement for capture of nucleic acids in accordance with an embodiment of the present disclosure. As a strand of nucleic acid (115) passes through a nanopore (110) of a solid-state membrane surface (120), indicated by way of a circular perforation, an electrode functionalized with a phosphate grabber (PG) (105) and an electrode (130) functionalized with a base grabber (BG) (125) form hydrogen bonds to 'hold' each nucleotide (115) as it is translocated through the solid state nanopore membrane (120). The combination of the two arrangements, phosphate and base grabbing, improves nucleic acid capture and translocation speed control for downstream analysis such as base sequence reading; grabbers on electrodes can also be used as mechanical clicks with controllable release via current modulation (e.g. bias voltages alter the non-bond interactions between the electrode functional groups and the DNA subgroups).

Strategic and specific placement of the electrodes in redundant, concentric, and symmetric arrangements allows enhanced capture and control. In particular, FIG. 1 shows a quadrupole arrangement, where the distribution of electric charge is among four equal electrodes that are spaced symmetrically around the nanopore. The number of electrodes placed around the nanopore is not limited to four, as more electrodes can be arranged in a similar manner, such as an octupole formation, to improve capture efficiency, motion control and reading resolution. The dielectric medium and minimum separation between any two electrode surfaces limits the total number of electrodes in the device. The distance between the grabbers is dependent on the molecules targeted for capture and translocation. For example, if ssDNA are the targeted molecules, the inter-electrode tip distances may have a 1.2-1.8 nm gap. For dsDNA, the inter-electrode tip distance may be 2.8-3.5 nm. Single-atom thick zigzag or armchair graphene nanoribbons (GNRs) may be used as electrodes, placed on the exposed surfaces of a solid-state nanopore membrane, or in a sandwich configuration between nanopore membrane slabs.

Figure 2A:
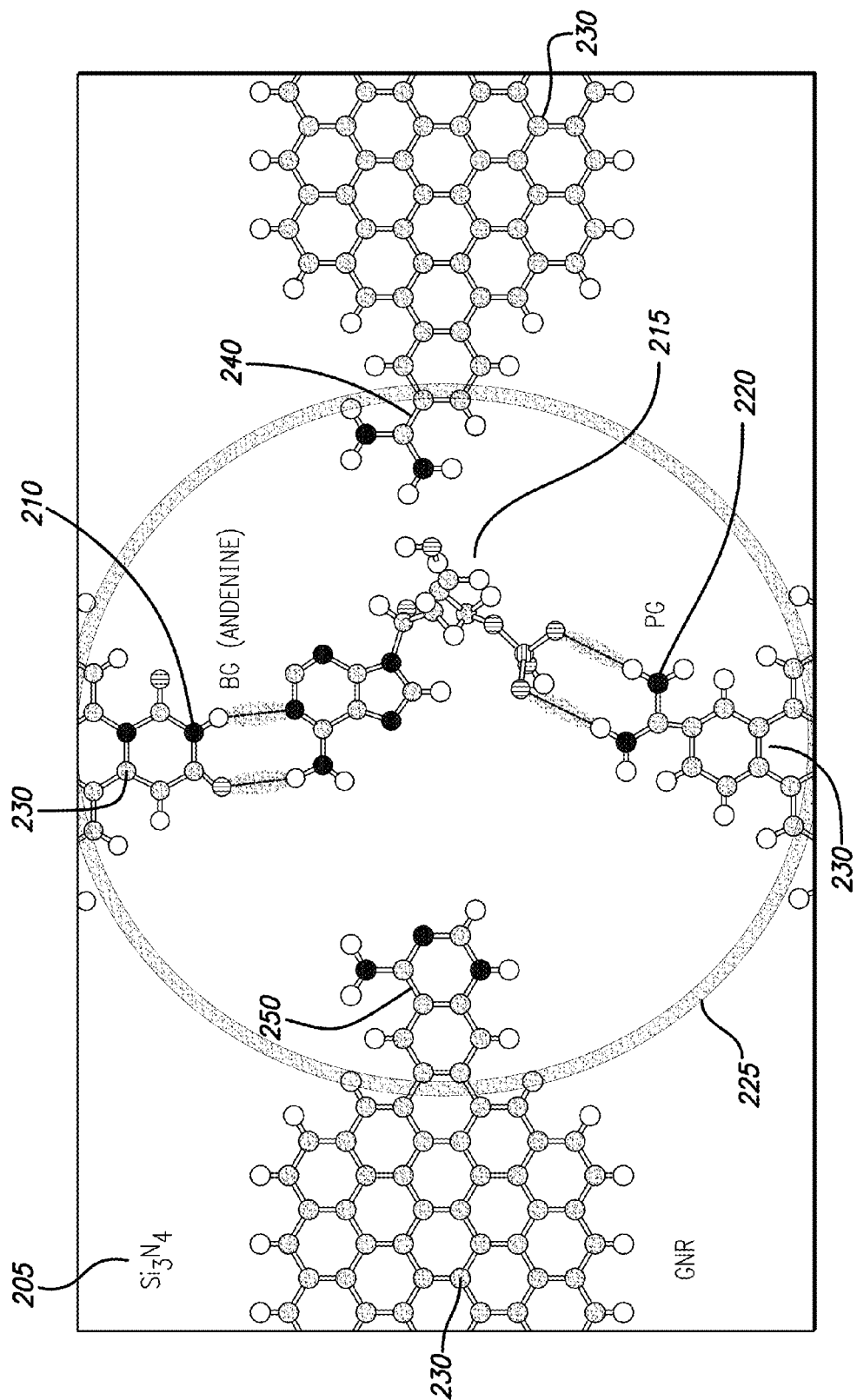
FIGS. 2A and 2B show an example of hydrogen bonding through the phosphate and base grabbers to ssDNA (single stranded DNA). In particular.

FIG. 2A is a schematic diagram illustrating capture of a single stranded adenine by phosphate and base grabbers functionalized to a set of four electrodes arranged in quadrupole. In this embodiment, a nanopore (225) is depicted as a circle perforation in a gray SiN solid-state membrane (205). The electrodes in this embodiment are graphene nanoribbons (GNRs) (230), as such materials possess good electronic conductive capabilities (both in its metallic zigzag and semiconducting armchair chiral forms). In particular, an adenine-specific phosphate grabber (220) and a base grabber (210) are each attached to opposing GNRs (230). The horizontal grabbers that are not capturing the adenine are a phosphate grabber (240) and a base grabber (250) specific to bonding with thymine. FIG. 2A exemplifies adenine (215) being captured by a hydrogen bonding specific to adenine and not thymine.

Figure 2B:
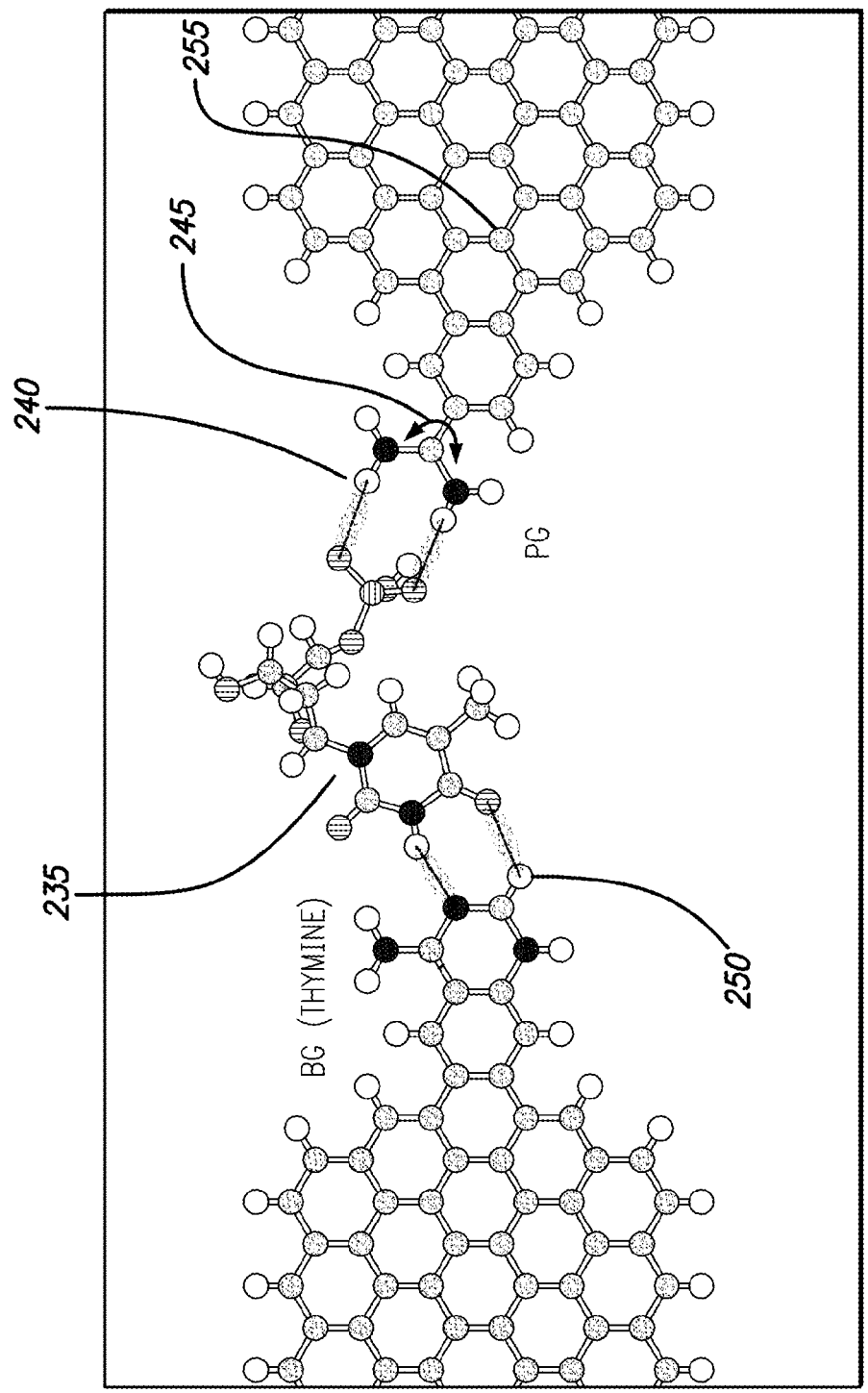

On the other hand, FIG. 2B illustrates the capture a single stranded thymine captured by a phosphate grabber and base grabber (full quadrupole electrode set not shown). This example removes depiction of a nanopore or membrane for simplicity, but still shows GNRs (255) functionalized with a phosphate grabber (240) and a base grabber (250) grabbing through hydrogen bonding a ssDNA Thymine (235). FIG. 2B also illustrates a single C—C covalent bond (245) that binds the GNR electrode (255) to phosphate grabber (240), thus providing a low-barrier angle-bend to enable proper H-bond alignment. Base grabbers can similarly be bonded to GNR electrodes with a C—C covalent bond as well.

The enhanced translocation control that FIGS. 2A and 2B illustrate lies in integrating a hydrogen bonding arrangement for i) capture, ii) translocation speed control, and iii) reduced signal-to-noise ratio in identifying translocating nucleobases through tunneling current signatures. As the ssDNA passes through the nanopore, all the electrodes are activated to generate a local electrostatic field. This field holds and aligns the DNA so that the electrodes with a relative positive charge attract the negative DNA backbone and electrodes with a negative charge repel the DNA backbone. In this embodiment, the generated electric field creates an electrostatic pull that brings the phosphate backbone groups (with a net negative charge) towards the phosphate grabber (220), and pushes the base towards the base grabber (210). Changing the state of the field (or word applied to all electrodes) allows that DNA to rotate and translocate through the pore in a screw-like motion.

The C—C covalent bond (245) allows the phosphate or base grabber to have a thermodynamically low-energy barrier rotation to improve coupling efficiently with the phosphate group of the nucleotide in the presence of thermal noise. Once the hydrogen bonds are formed between the DNA/RNA molecules and the corresponding grabber, an enhanced electrical circuit is formed. With complete hydrogen bonding between the electrodes and the DNA, the susceptibility to thermal vibrations is reduced and the transmission spectrum for the molecular junction (e.g., conductivity) is enhanced.

As a base or base pair translocates electrophoretically through the nanopore and completes the circuit illustrated in FIG. 2A, the conductance through the molecular junction is measured. Because each nucleotide or base pair has a distinct electron tunneling signature, nucleotides can be identified as they pass through the nanopore, including but not limited to modified or mutated bases OxoG or CpG dinucleotides. Thus, the H-bonding in this embodiment not only improves the alignment and thermal stability of the molecules as they pass through a nanopore, but also improves the signal-to-noise-ratio of base sequence reading through electron tunneling.

In an embodiment where ssDNA is being translocated, a minimum of two sets of quadrupole electrodes and grabbers, with tips radially separated by a gap of, e.g., 1.2-1.8 nm, are provided, where a first set of functionalized electrodes handles the adenine-thymine (A-T) group and corresponding phosphate groups, and the other set of functionalized electrodes handles the cytosine-guanine (C-G) group with its corresponding phosphate group. The two sets are placed apart along the translocation direction within the nanopore or on either of a solid-state membrane surface (e.g., nanopore axis). A-T and C-T electrodes do not need to be separated by a multiple of the inter-base distance, which is approximately 0.33 nm in ssDNA. Very thin membranes such as graphene sheets require a support structure up to a few tens of nanometers thick. The thickness of the membrane affects the DNA capture potential barrier, requiring scaling of the voltage bias threshold.

Figure 3:
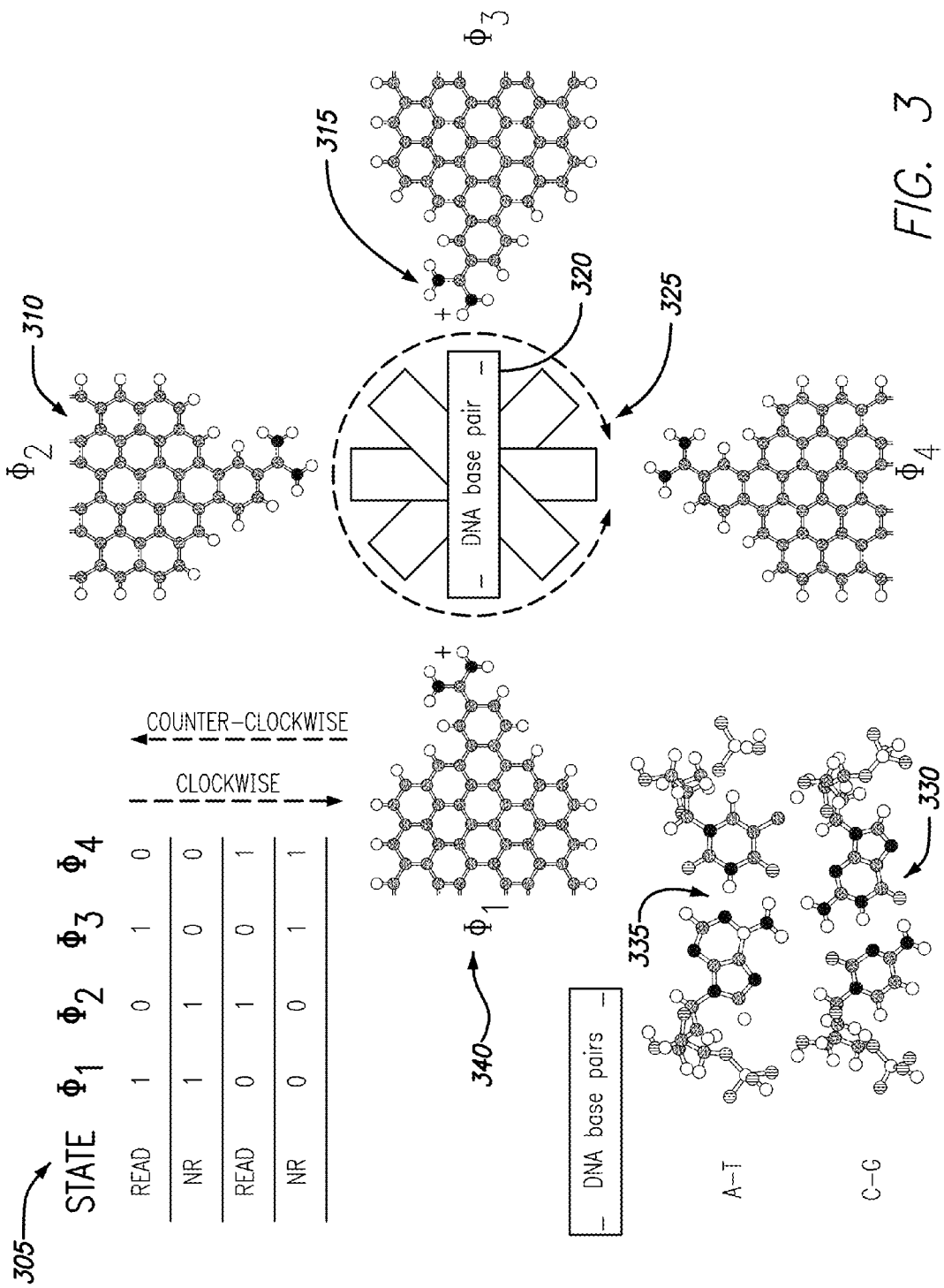
FIG. 3 shows an arrangement of phosphate grabbers on a nanopore configured to capture dsDNA (double stranded DNA), a structural representation of the A-T and C-G base pairing, and a table of logic voltage sequences (where logic 0 represents a ground or negative voltage state and logic 1 represents a positive voltage) to the electrode phases.

FIG. 3 illustrates capture and rotation of dsDNA (320) through a nanopore (325) with an arrangement of four functionalized GNR electrodes (310). In dsDNA, hydrogen bonding occurs between bases of complementary nucleotides: A-T (or T-A) (335) or C-G (or G-C) (330). Therefore, the only available atoms that can participate in hydrogen bonding are located on the phosphate groups of the nucleotides. Thus, embodiments of the present disclosure where dsDNA is to be translocated only require phosphate grabbers (PGs) (315).

For dsDNA, only one set of electrodes in quadrature (or octagonal setup) is needed. Any electrode pair then achieves recognition of the A-T (or T-A) base pair or C-G (or G-C) base pair. Electrode pairs can also identify mismatched base pairs (e.g. A-G or C-T) or modified base pairs based on the unique tunneling signature for each nucleic acid. By way of example and not of limitation, the electrode nanogap can be 2.6-3.0 nm in length. Phosphate grabbers utilize hydrogen bonding to stabilize the translocating dsDNA and to improve readability through tunneling currents as already described for FIGS. 2A (220) and 2B (240) for ssDNA.

Rotary stepper-motor phase sequence can be achieved by controlling the voltage bias word applied to the electrodes, the sequence of presentation would determine the direction, and rate of word change on the electrodes would determine the speed of rotation as depicted in the inset table of FIG. 3 (305). Stepwise rotation of the helix can be promoted through selective voltage sequences to the electrode phases (340) and may be controlled in fractions of full steps to improve rotational resolution (e.g. partial rotation between phases). Additionally, the direction of translocation can be reversed by inverting the electrode word presentation sequence. In particular, FIG. 3 shows capture/reading steps ('Read') combined with rotation steps ('NR'). In a reading step, alignment of the captured base pair is kept by activating two opposite (non-contiguous) phosphate grabbers (e.g., $\phi_1$ and $\phi_3$=1). On the other hand, in an NR step, rotation is induced by activating two contiguous phosphate grabbers (e.g., $\phi_1$ and $\phi_2$=1). Though base reading occurs only when the DNA base-pair is effectively placed between two existing electrodes, partial rotations allow translational motion of the strand through the nanopore.

Figure 4A:
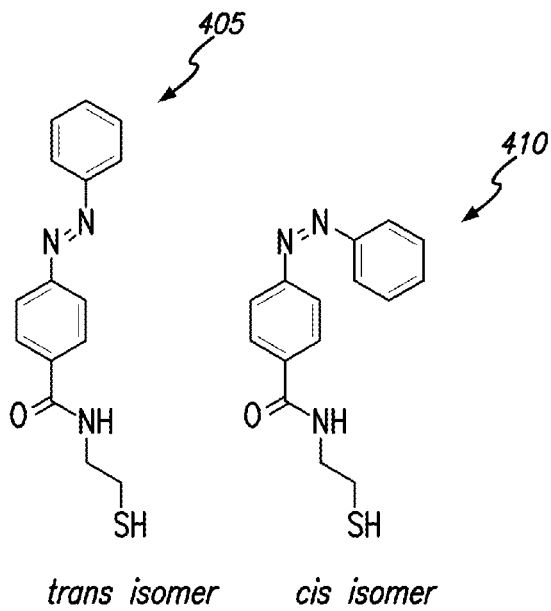
Figure 4B:
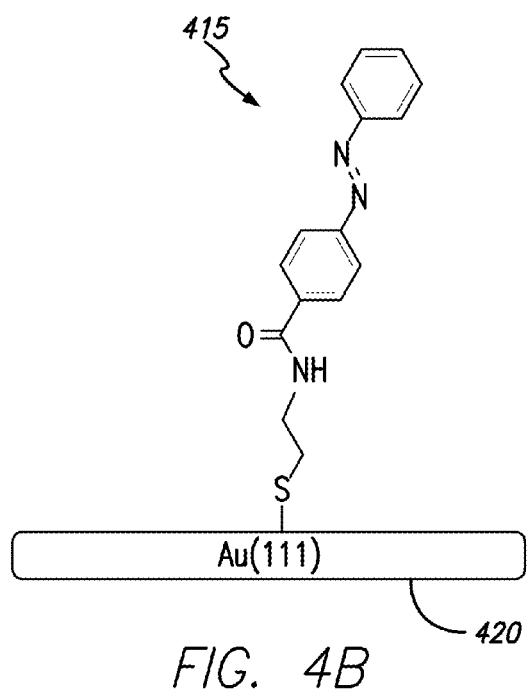
Figure 5:
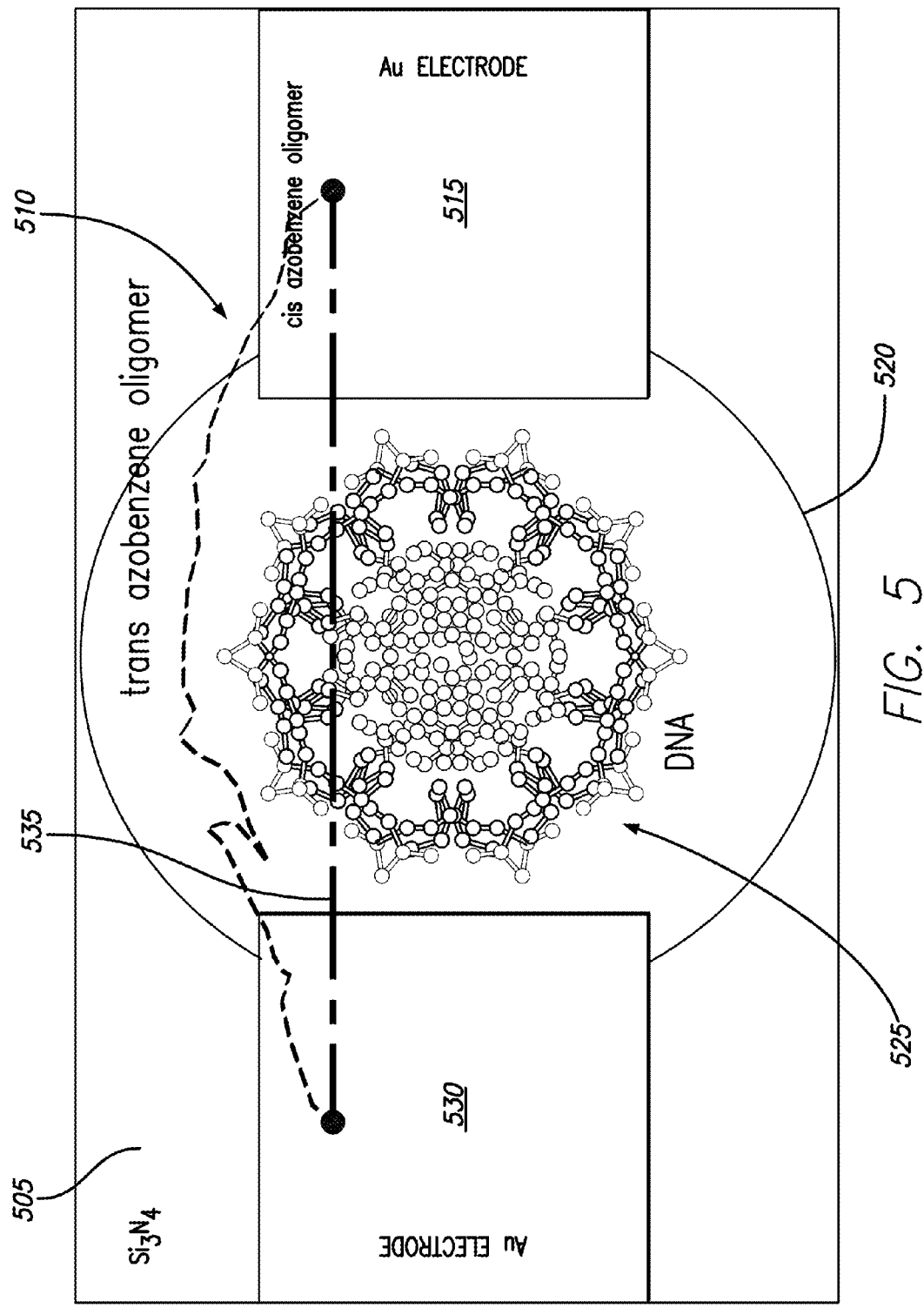
FIG. 5 shows a top view of a nanopore/oligomer arrangement with cis- and trans-photo-activated azobenzene oligomer selectively controlling the translocation of the DNA molecule into the plane.

FIG. 4 and FIG. 5 exemplify an embodiment for a molecular ratchet-type translocation controller, another mechanism in accordance with the present disclosure to block and control the flow of nucleic acids through a nanopore. In particular, by using a specific photoactivated contractile oligomer functionalized across the nanopore, the oligomer acts as a molecular ratchet which can regulate the flow of translocating nucleic acids. The oligomer should be long enough to stretch outside a nanopore when expanded and invade the pore when contracted. The switch between oligomer states is controlled by feedback form the nanopore device's ionic current signal.

Specifically, FIGS. 4A and 4B illustrate a compound, azobenzene, which can be used as a molecular ratchet. Azobenzene is a fast light-controlled photoisomerizable compound that can oligomerize and can be used as a van der Waals translocation regulator. 12 azobenzene subunits (about 12.2 nm in length) have an estimated contractile potential of about 1.5 nm, the expected radius of the nanopore. FIG. 4A illustrates two stereoisomers, specifically geometric isomers of azobenzene: trans (405) and cis (410). The nitrogen-nitrogen double bond in azobenzene undergoes a reversible trans/cis photoisomerization under frequency selective irradiation (e.g., a 365 nm wavelength results in cis conformation, while a 436 nm wavelength results in trans isomer) and in picoseconds leading to its effective contraction/extension. FIG. 4B illustrates azobenzene (415) anchored to a metallic gold surface from an electrode (Au111) (420).

FIG. 5 illustrates a top view of a nanopore/oligomer arrangement in accordance with an embodiment of the present disclosure, showing a cis azobenzene configuration (535) limiting the translocation of a nucleic acid molecule such as DNA (525) into the plane (mainly through non-bond van der Waals interactions) and a trans azobenzene isomer releasing (510). In this embodiment, the oligomer is placed diametrically between two electrodes (515, 530), thus spanning across nanopore (520). The oligomer anchor sites are off-centered with respect to nanopore (520), depicted as a circle in a SiN membrane (505), and can be functionalized to be either on the electrodes or on the substrate. A light source (not shown) can be used to control the cis and trans states of the oligomer.

In this configuration, the oligomers act as photoisomerizable tendon to block or enable molecular translocation through the nanopore in a two-electrode molecular junction solid-state nanopore sequencing device configuration. Transitions in the ionic current across the nanopore can provide appropriate feedback signals to detect when a new base is entering the nanopore (with improved resolution for thinner membranes). In other words, the ionic current serves to control the radiation frequencies to selectively alternate between the trans/cis isomerization states, giving stop-go-stop single base control and precision of translocation. Similar to the grabber arrangement shown in FIGS. 2A and 2B, nucleotides can be identified when the molecule passes between the two electrodes by the unique changes in the amplitude of the tunneling current for each nucleotide. Because the oligomer adds mechanical stability to the translocating nucleobases, the signal-to-noise ratio is improved for subsequent base reading even in the absence of actual bonding between the electrode and the nucleobases. The oligomeric molecular ratched and the grabber arrangement previously described can be used together to further improve the signal-to-noise ratio.

Figure 6A:
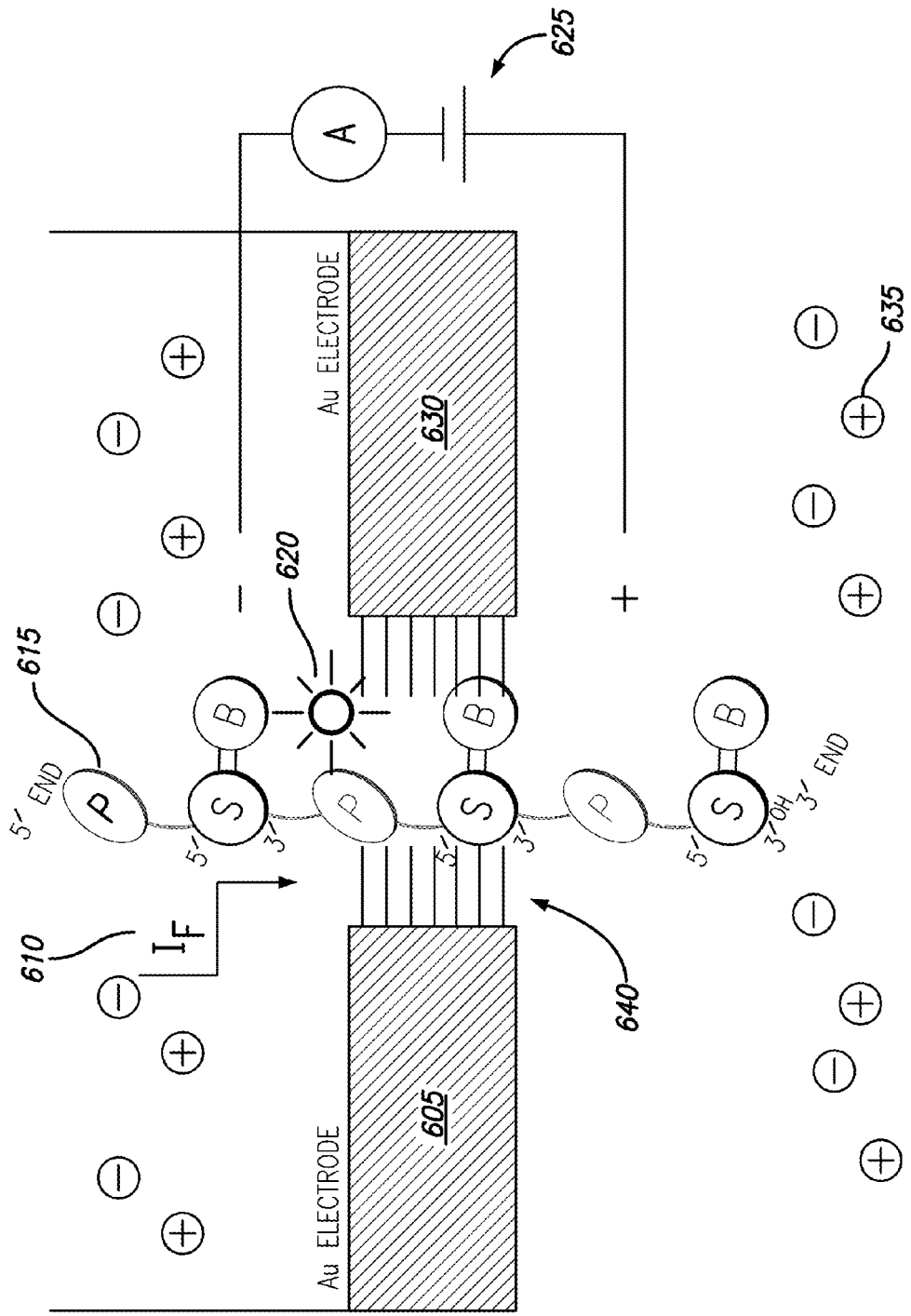
FIGS. 6A and 6B shows implementation of an array of azobenzenes functionalized to the intra nanopore-exposed surface. The corresponding functionalized surface can be that of the electrodes (e.g. gold surface), the solid-state pore walls (e.g. SiN), or both. In particular.
Figure 6B:
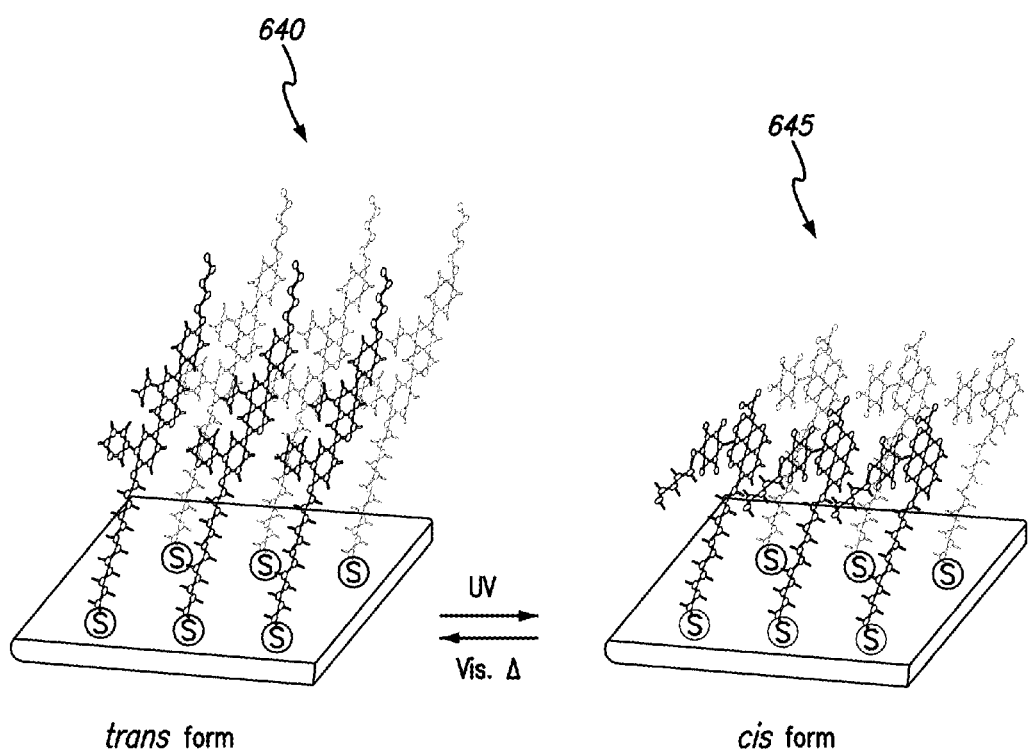

FIGS. 6A-B illustrates use of an array of photoisomerizable molecules functionalized in the nanopore/electrode walls to modulate single-base ssDNA/RNA translocation through a nanopore device. Similarly to FIGS. 4 and 5, the embodiment in FIG. 6A implements azobenezene as an exemplary compound whose conformation is radiation-frequency dependent. However, this embodiment utilizes an array of monomers that functionalize the intra-pore exposed metal surface of each electrode as opposed to a polymer that stretches across a nanopore. In accordance with the embodiment of FIG. 6B, the changes in the pore/electrode wall surface morphology from trans-azobenzene cause steric clashes and increased hydrophobicity (via reduced surface energy and increased roughness), which will directly hinder the translocation of molecules through the nanopore.

In the embodiment of FIG. 6A, azobenzene is lined up the walls of each electrode (605, 630) in the nanopore device. Molecules like ssDNA (615), comprising of a string of sugars (S), bases (B), and phosphates (P), are suspended in an ionic solution (635). An applied bias voltage (625) promotes electrophoretic movement of ssDNA, and the ssDNA follows the same direction as the current (610). Azobenzene can exist either as a longer trans molecule (640) or as a shorter cis molecule (645). Since azobenzene is photoreactive and is functionalized on the walls of the electrode, a light source (620) can be embedded in the solid-state device to switch between the isomeric states of the array of azobenzene molecules. Under visible light source (620) at 436 nm, the trans form (640) isomerization will reduce the effective nanopore diameter, thereby limiting the translocation of molecules through the nanopore, while at 365 nm UV the cis-form (645) enhances translocation. The isomerization times are much faster than the translocation rate requirements for a nanopore device, enabling per-base control through ionic current blockage feedback. Also, nucleobases can be identified through tunneling signatures as the molecule passes through a nanopore.

FIGS. 7A-7C illustrate a chemical-free, dented atomic-resolution nanodevice or "nanoshuttle" to translocate molecules like ssDNA or ssRNA. The nanoshuttle described herein is a piezoelectrically controlled linear stepper nanomotor. An actuator (not shown) can be coupled to the nanoshuttle. Actuation currents versus shuttle displacement and frequency of operation can be determined from the fabrication process and materials used and the operation environment of the nanodevice. The nanoshuttle moves perpendicular to the translocation direction as depicted in FIG. 7A, where the translocation direction is shown as vertical bottom-up direction, while the movement of the nanoshuttle is in a left-right-left direction. As shown in FIG. 7A, the nanoshuttle device comprises a plurality of teeth or dents (720, 730) to direct movement of molecules. To fabricate the plurality of dents for atomic resolution in a nanoshuttle, high resolution etching techniques, such as low energy electron enhanced etching (LE4), can be employed on silicon substrates.

FIG. 7A shows a top view of the nanoshuttle. Reference sign (L4) indicates the groove within the silicon substrate over which the nanoshuttle moves, providing a support surface for the nanoshuttle. Reference numeral 705 of FIG. 7A shows the outline of the nanoshuttle, which can be made, for example, of silicon-based or other non-conducting solid-state material.

Reference numerals (710) and (715) of FIG. 7A indicate the highest regions flanking the dented path when looking from a top view perspective. Reference numeral (720) indicates a lowered, intermediate point and the walls of the dents between which the molecules are allowed to pass. Reference numeral (725) indicates the bottom of the etched dented path, which corresponds to the lowest topographical region of the nanoshuttle, defining an internal channel or path inside which the molecules are allowed to move under the constraining geometry.

With continued reference to FIG. 7A, an exemplary ssDNA general translocation path would be as follows: a molecule would start in the nanoshuttle at the position marked (1); then the nanoshuttle moves left forcing the same molecule to move towards position (3), via (2), by non-bond repulsive interactions with the dented walls; the nanoshuttle would then return to the right position forcing the molecule to position (5), via (4), and so on. Continued right-to-left shuttle cycles would cause the ssDNA to translocate upwards. An ionic current in the translocation would enhance the overall motion of the ssDNA.

This general path would continue through the dented nanoshuttle until the molecule has passed through the entire length of the shuttle. In case of single-stranded nucleic acids moving through the nanoshuttle dented path, as the one shown in the figure, a lower limit for the pitch between the nanoshuttle's teeth can be set, for example, to the DNA/RNA's distance between adjacent bases, i.e. about 0.33 nm, though it may be a higher multiple of the inter-base distance. Reference signs B1, B2, and B3 of FIG. 7A represent respective locations where the bases of three nucleic acids would be relative to each other as a molecule moves along the nanoshuttle. In accordance with the nanoshuttle embodiment of FIG. 7A, an ionic current (735) flowing in the translocation direction may or may not be present. However, presence of an ionic current is expected to improve ssDNA capture.

FIG. 7B illustrates a cross sectional view along the central vertical dotted line of FIG. 7A, shown in a side-to-side arrangement with reference to FIG. 7A. Here, reference numeral (750) shows the outline of the nanoshuttle, reference number (760) shows the bottom of the dented path, reference sign (B) represents the base of nucleic acid, reference sign (S) represents the sugar of a nucleic acid, and reference sign (P) represents the phosphate of a nucleic acid, while reference numeral (745) represents the ester bond that chemically connects that sugar and phosphate groups of a nucleic acid. This view shows that the sugar-phosphate backbone of the nucleic acid is higher topographically than the base as it passes through the nanoshuttle.

In this view, a graphene nanoribbon (GNR) (750) overlaid on top of the shuttle can also be seen. GNRs constrain the translocation of molecules to within the chambers of the nanoshuttle according to the present disclosure. Similar to the identification of bases via the tunneling current previously described, the GNR may provide a means for nucleobase identification as well. When a bias voltage is applied to the GNR, it stimulates electric conduction. Molecules that are near the surface can alter the way electrons flow through it, thereby changing its transmission spectra. Since each base (e.g. A, T, C, G, or U) alters the transmission spectra in a distinct manner like tunneling signatures, the changes in the transmission spectra can identify which nucleotides are translocating through the nanoshuttle. The changes in conductance of the nanoribbon as a result of its interactions with the nucleobases via p-p stacking are used to identify the translocating nucleobase. In accordance with an embodiment of the present disclosure, identification via the field effect change caused on the GNR can be achieved through data-mining and two-dimensional transient autocorrelation analysis.

FIG. 7C illustrates a front view of the embodiment shown in FIGS. 7A and 7B, where the sugar (S) and base (B) can be seen moving left or right inside the dented path (760). Also shown in FIG. 7C is the graphene nanoribbon component (750) already discussed in FIG. 7B.

Figure 8A:
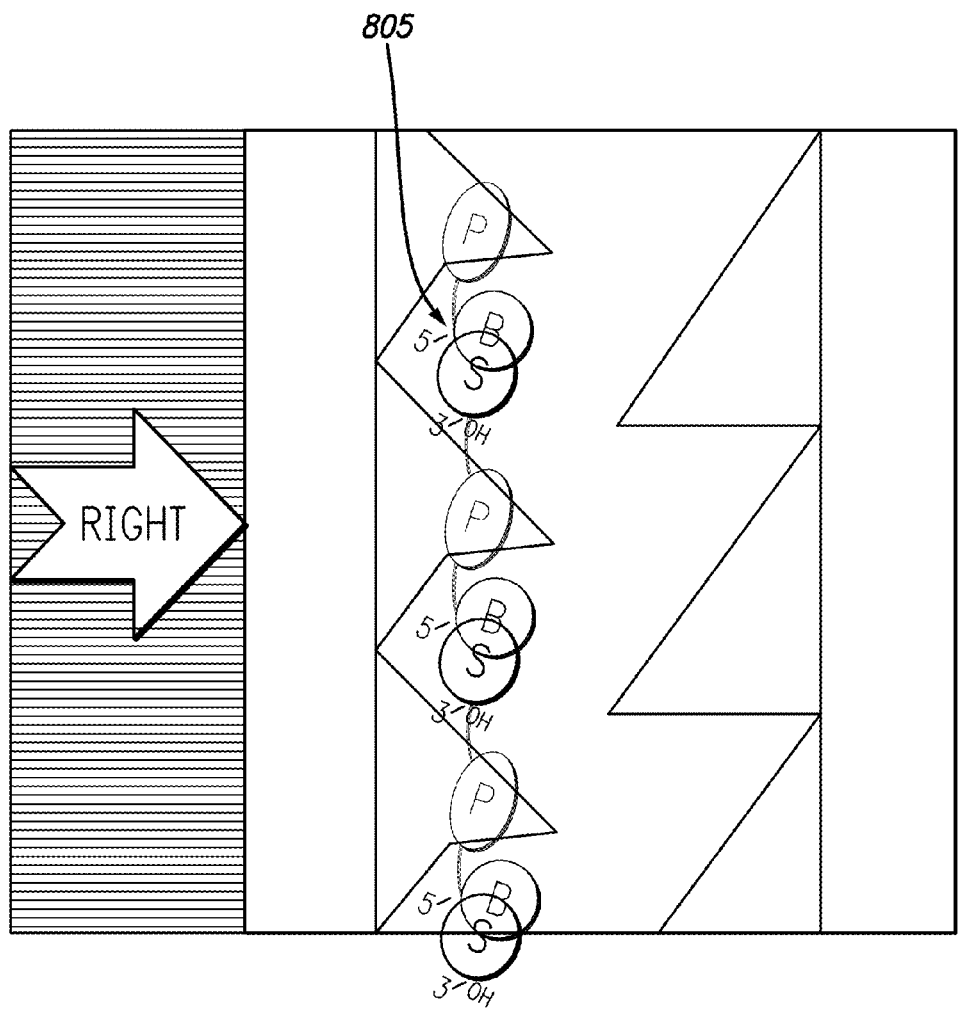
FIGS. 8A-8C show a sequence of ssDNA translocation steps through the piezoelectric nanoshuttle of FIGS. 7A-7C.
Figure 8B:
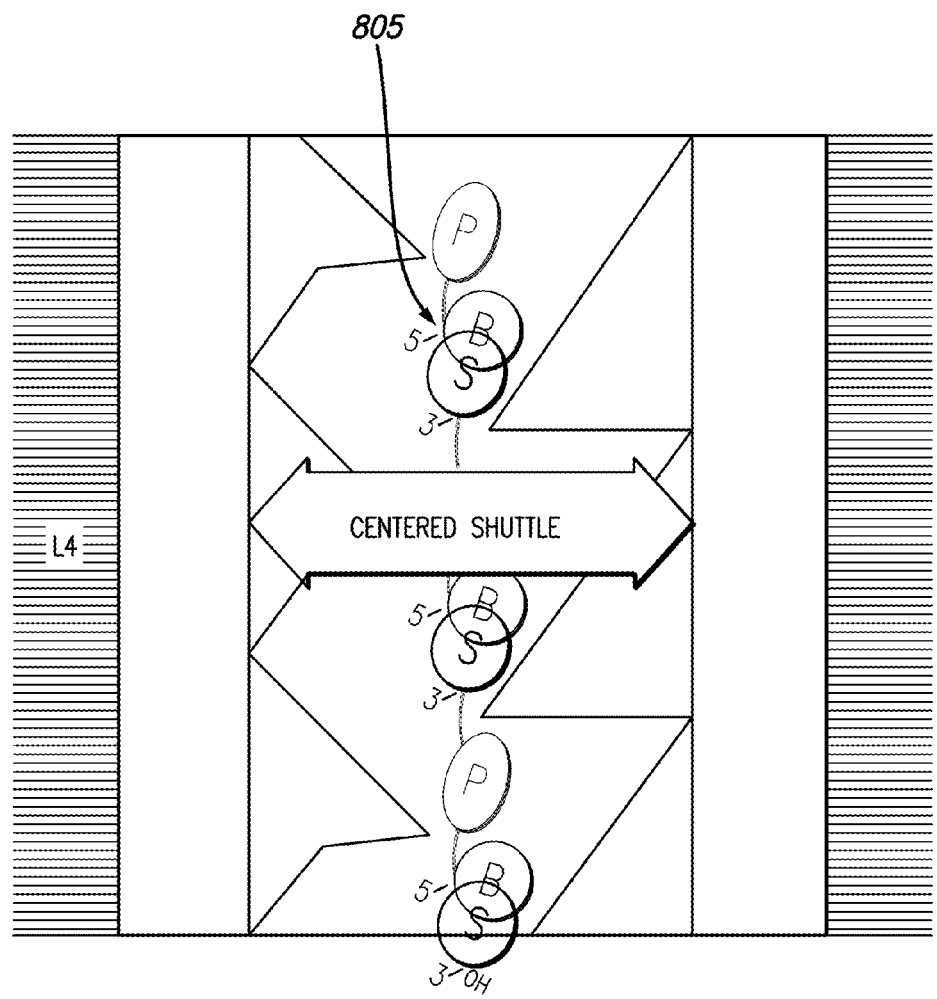
Figure 8C:
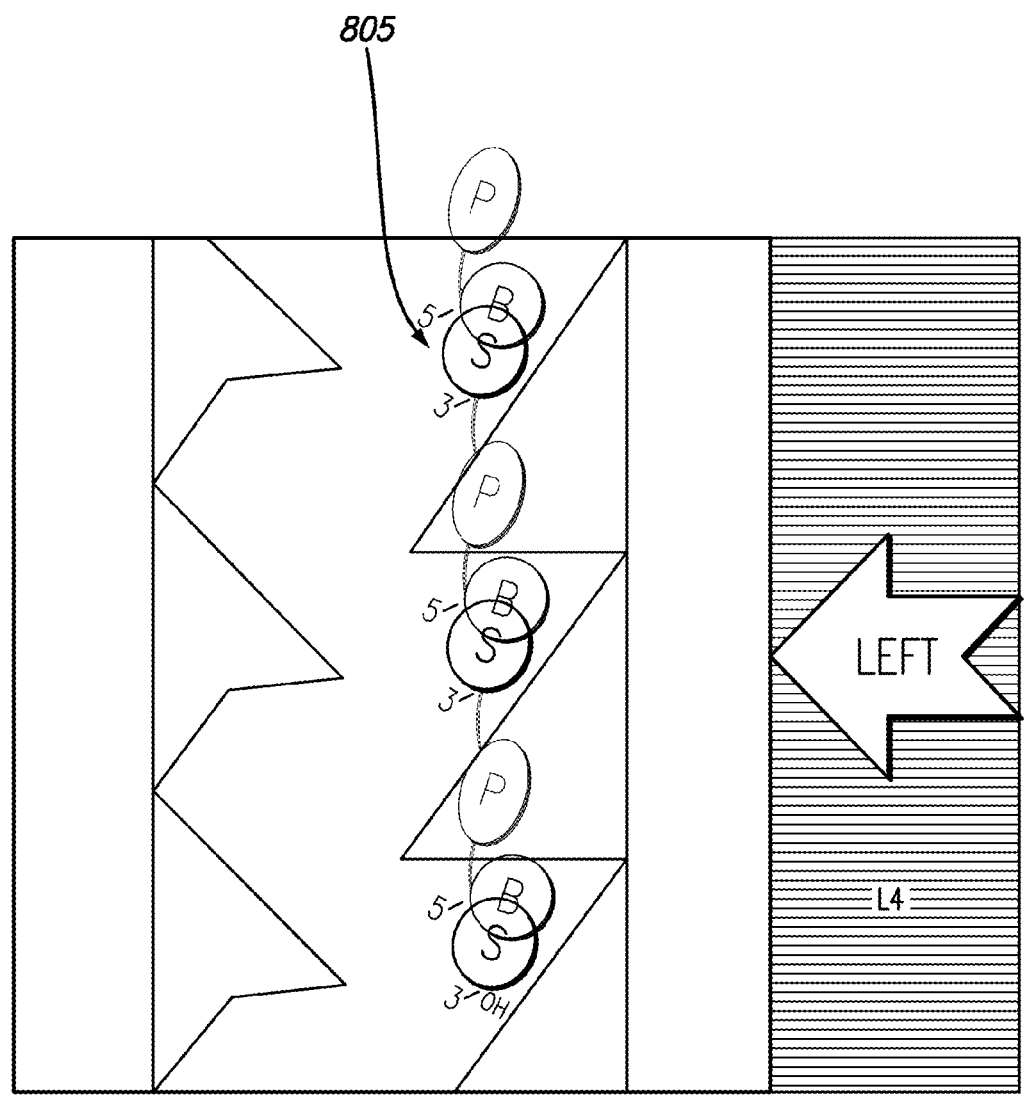

Similarly, FIGS. 8A-8C illustrate an ssDNA (805) translocation sequence through the nanoshuttle shown in FIGS. 7A-7C from entry to exit, in accordance with positions (1)-(5) explained above with reference to FIG. 7A. In particular, FIG. 8A corresponds to positions (1) and (5) of FIG. 7A, FIG. 8B corresponds to positions (2) and (4) of FIG. 7A, while FIG. 8C corresponds to position (3) of FIG. 7A.

Figure 9:
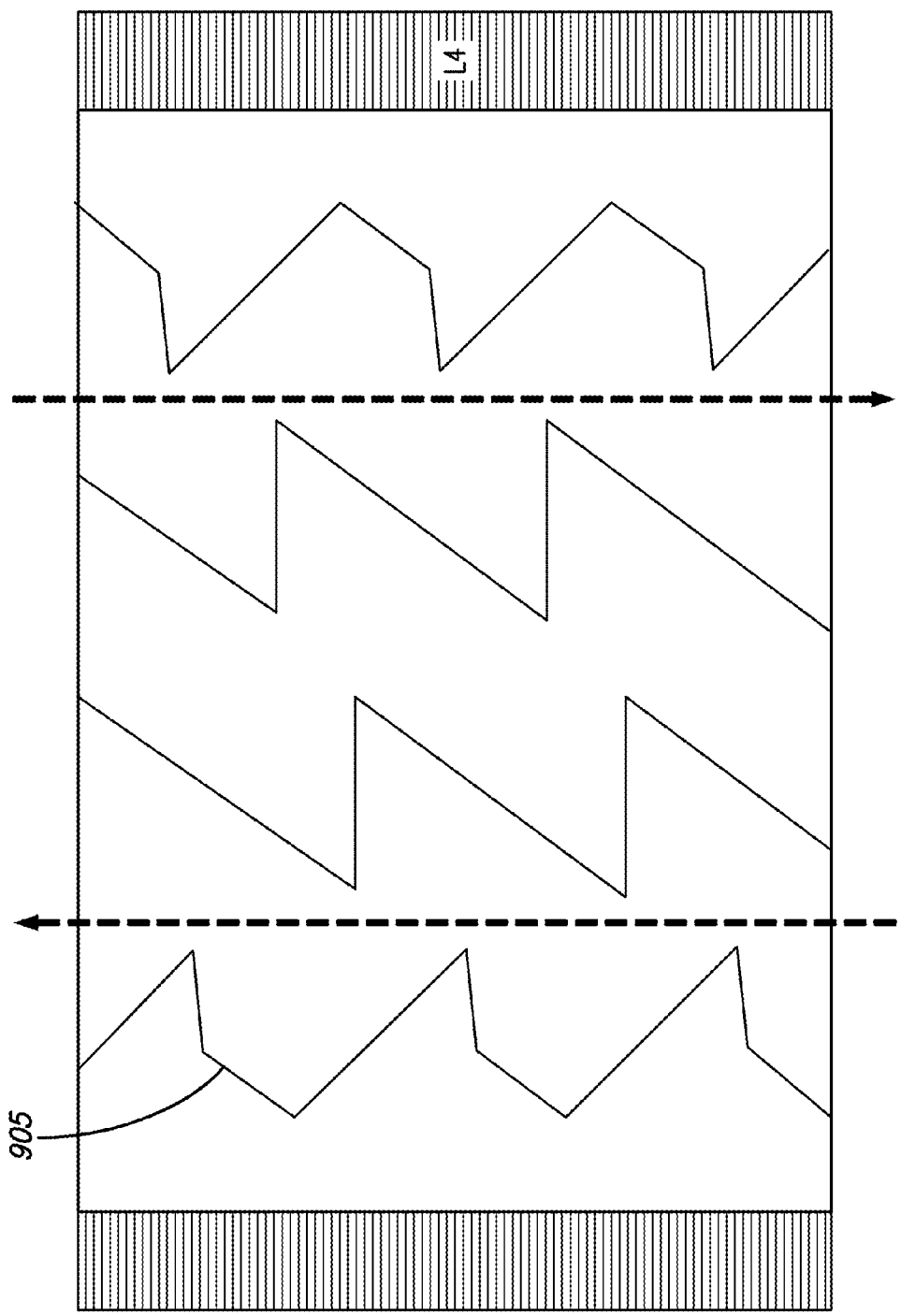
FIG. 9 shows a modified piezoelectric nanoshuttle further comprising a complementary and vertically flipped mirrored set of teeth.

While the nanoshuttle device shown in FIGS. 7A-7C and FIGS. 8A-8C allows translocation in a bottom-to-top direction according to the vertical arrow shown in FIG. 7A, FIG. 9 shows an embodiment where bidirectional translocation control is provided. In such embodiment, the nanoshuttle device further comprises a complementary and vertically flipped mirrored set of left gear teeth (905). Also, the present disclosure also provides embodiments where the nanoshuttle design can be made longer in the translocation direction for improved efficiency.

While the embodiments of FIGS. 7A-7C, FIGS. 8A-8C, FIG. 9 only show a single nanoshuttle, the person skilled in the art will readily understand that arrays on nanoshuttle devices (e.g. parallel arrays) can also be devised in accordance with the present disclosure. By way of example, such arrays can be fabricated by way of nano-electro-mechanical (NEM) processing techniques on silicon wafers for ultra-high throughput sequencing devices.

The examples set forth above are provided to give those of ordinary skill in the art a complete disclosure and description of how to make and use the embodiments of the translocation and nucleotide reading mechanisms for sequencing nanodevices of the disclosure, and are not intended to limit the scope of what the inventors regard as their disclosure. Modifications of the above-described modes for carrying out the disclosure can be used by persons of skill in the art, and are intended to be within the scope of the following claims.

All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a", "an", and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The invention claimed is:

1. A device to translocate molecules, comprising:
a first molecule channel along which translocation of the molecules is adapted to occur along a first direction; and
a first set of teeth jointly moveable back and forth in a same teeth direction substantially perpendicular to the first direction, wherein joint movement back and forth of the first set of teeth in the same teeth direction causes the translocation of the molecules in the first molecule channel along the first direction.

2. The device of claim 1, wherein the teeth of the first set of teeth are located sideways of the first molecule channel.

3. The device of claim 1, further comprising a first conductive material located above the first molecule channel and the first set of teeth along an extension of the first molecule channel.

4. The device of claim 1, the device being made of silicon or other silicon-based non-conducting material.

5. The device of claim 1, further comprising:
a second molecule channel along which translocation of the molecules is adapted to occur along a second direction opposite the first direction; and
a second set of teeth moveable back and forth in the teeth direction together with the first set of teeth, wherein movement back and forth of the first set of teeth and the second set of teeth causes translocation of the molecules in the second molecule channel along the second direction.

6. The device of claim 1, wherein the first molecular channel has a pore size and the pore size remains substantially unchanged during joint movement back and forth of the first set of teeth.

7. The device of claim 1, wherein an ionic current is present in the first direction.

8. The device of claim 2, wherein the teeth of the first set of teeth located on a first side of the first molecule channel have a triangular shape.

9. The device of claim 2, wherein the teeth of the first set of teeth located on a first side of the first molecule channel are asymmetric with the teeth on a second side of the first molecule channel opposite the first side.

10. A device to translocate molecules, comprising:
a first molecule channel along which translocation of the molecules is adapted to occur along a first direction;
a first set of teeth moveable back and forth in a teeth direction substantially perpendicular to the first direction, wherein movement back and forth of the first set of teeth in the teeth direction causes the translocation of the molecules in the first molecule channel along the first direction; and
a first conductive material located above the first molecule channel and the first set of teeth along an extension of the first molecule channel.

11. A device to translocate molecules, comprising:
a first molecule channel along which translocation of the molecules is adapted to occur along a first direction;
a first set of teeth moveable back and forth in a teeth direction substantially perpendicular to the first direction, wherein movement back and forth of the first set of teeth in the teeth direction causes the translocation of the molecules in the first molecule channel along the first direction;
a second molecule channel along which translocation of the molecules is adapted to occur along a second direction opposite the first direction; and
a second set of teeth moveable back and forth in the teeth direction together with the first set of teeth, wherein movement back and forth of the first set of teeth and the second set of teeth causes translocation of the molecules in the second molecule channel along the second direction.

* * * * *